(12) United States Patent
Gantt et al.

(10) Patent No.: US 6,770,090 B2
(45) Date of Patent: Aug. 3, 2004

(54) ANATOMICALLY CURVED GRAFT FOR IMPLANTATION AT THE AORTIC ARCH

(75) Inventors: Samuel Gantt, Lodi, NJ (US); Bruce Fieggen, Wayne, NJ (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 10/020,267

(22) Filed: Dec. 7, 2001

(65) Prior Publication Data

US 2003/0109919 A1 Jun. 12, 2003

(51) Int. Cl.[7] .................................................. A61F 2/06
(52) U.S. Cl. ........................ 623/1.35; 623/1.51; 623/12
(58) Field of Search ................................ 623/1.1, 1.13, 623/1.23, 1.28, 1.49, 12, 1.51–1.53; 604/7, 8; 606/151, 153, 155, 156, 158, 191, 192, 194, 195, 198; 600/16, 36, 37

(56) References Cited

U.S. PATENT DOCUMENTS

| | | | |
|---|---|---|---|
| 4,798,606 A | * | 1/1989 | Pinchuk ...................... 623/1.1 |
| 5,904,714 A | | 5/1999 | Nunez et al. |
| 6,039,183 A | | 3/2000 | Rudnick et al. |
| 6,187,033 B1 | | 2/2001 | Schmitt et al. |
| 6,499,487 B1 | * | 12/2002 | McKenzie et al. .......... 128/898 |
| 6,685,625 B2 | * | 2/2004 | Gabbay ........................ 600/36 |

FOREIGN PATENT DOCUMENTS

| | | | |
|---|---|---|---|
| WO | WO 95/03754 | 2/1995 | |
| WO | WO 9503754 A1 | * 2/1995 | ............. A61F/2/06 |

OTHER PUBLICATIONS

U.S. patent application Ser. No. 09/556,671, filed Apr. 24, 2000, Inventor: Michael Austin, "Anatomically Correct Endoluminal Prostheses".

* cited by examiner

Primary Examiner—David J. Isabella
Assistant Examiner—Urmi Chattopadhyay
(74) Attorney, Agent, or Firm—Hoffmann & Baron, LLP

(57) ABSTRACT

An implantable textile prosthesis which is anatomically curved to substantially match the natural curvature of the aortic arch in a human being or patient is provided. The first woven section is arched define an apical region and to conform generally to an aortic arch of a human patient. A plurality of elongate woven tubular extents extend vertically from a top wall portion at the apical region of the tubular main wall. These tubular extents are sutured to the first woven section to provide fluid communication between the tubular main wall and the tubular extents.

12 Claims, 6 Drawing Sheets

ANATOMICALLY CURVED GRAFT FOR IMPLANTATION AT THE AORTIC ARCH

FIELD OF THE INVENTION

The present invention is directed generally to a vascular prosthesis which is useful in repair or replacement of a branched section of a blood vessel. More particularly, the present invention provides a textile vascular graft which is particularly useful in branched end-to-side anastomoses of the aorta and its arterial branches.

BACKGROUND OF THE RELATED TECHNOLOGY

The use of tubular textile fabrics for soft-tissue implantable prostheses is well known in the repair or replacement of damaged or diseased lumens in the body. For example, tubular devices or conduits are used to repair lumens such as in the esophagus and colon areas, and, in particular, prostheses are used in the vascular system to repair, buttress or replace a weakened section of the vessel. Such conduits are generally affixed in a specified location in the vessel by means of sutures, stents, hooks or other mechanisms which serve to secure the device in place.

Synthetic vascular grafts for the repair or replacement of blood vessels have taken a wide variety of configurations and shapes. The most common type of vascular graft is that manufactured in a generally tubular form extending along a relatively straight longitudinal axis. Such tubular vascular grafts are particularly well suited for use in end-to-end anastomoses, i.e., where the damaged portion of the blood vessel is dissected and the ends of the tubular graft are connected to the cut ends of the blood vessel to span the dissected portion. These tubular grafts may also be used in end-to-side anastomoses, i.e., where the end of a blood vessel is attached to the side of a graft tube or where the end of a graft tube is attached to the side of a blood vessel. Such tubular vascular graft configurations are also useful in endovascular applications, where the graft is inserted percutaneously and is positioned to span a damaged or diseased portion of a blood vessel without conventional surgery.

For branched end-to-side anastomoses of the aorta and its arterial branches it is necessary to provide an end-to-side vascular graft in which the side branch portion extends substantially perpendicular from the main portion to replace a portion of a blood vessel or to be positioned within a portion of a vessel which splits into one or more branch vessels. One such conventional graft is an aortic arch graft 10 shown in FIG. 1. Graft 10 includes an elongate main tube 12 and a plurality of aligned branch tubes 14 extending from the main tube 12 in generally parallel fashion. In certain situations where the aortic arch graft is designed to be temporarily connected to external devices, such as for example, a heart-lung machine, the graft 10 may include a lateral branch 16 extending from main tube 12 at a location spaced from the aligned branches 14.

Such end-to-side vascular grafts have typically been constructed by suturing one tubular vascular graft to the side of a second tubular vascular graft. Such end-to-side vascular grafts are used, for example, to repair or replace a damaged or diseased portion of the aorta. In such procedures, an aortic vascular prosthesis which includes a main aortic trunk portion and arterial branch portions extending generally perpendicular to the main aortic trunk portion for the left and right carotid arteries and the subclavian artery is particularly well suited. In order to provide an aortic vascular prosthesis with three branches, a surgeon will typically suture three separate straight tubular vascular grafts to the side of a larger tubular graft. Such suturing, however, usually occurs immediately prior to or during a procedure, is labor intensive and requires extreme skill and precision in suturing, thereby introducing the potential for human error.

Prior art end-to-side vascular grafts, such as the aforementioned aortic vascular prostheses, have not been completely successful. In particular, it has been sometimes difficult to correctly position the graft at the aortic arch region because the prior art grafts have been substantially straight or just slightly arched while the aortic arch is substantially curved. Furthermore, prior art grafts typically kinked when deformed or bent to a curve which anatomically contours the curvature of the aortic arch. Such kinking further complicates the placement of the graft during surgery.

Accordingly, there is a need for a vascular graft which has a configuration more favorable for implantation at the aortic arch region and which can better conform to the natural curvature of the aortic arch in a human. Furthermore, there is a need for a vascular graft which does not kink and which maintains a fully open lumen when shaped to the natural curve of the aortic arch.

SUMMARY OF THE INVENTION

The present invention is an implantable textile prosthesis which is anatomically curved to substantially match the natural curvature of the aortic arch in a human being or patient. The prosthesis has a first woven section having an elongate tubular main wall having a first and a second open end defining a fluid passageway therethrough. The first woven section is arched to define an apical region and to conform generally to an aortic arch of a human patient. A plurality of elongate woven tubular extents extend vertically from a top wall portion at the apical region of the tubular main wall. These tubular extents are sutured to the first woven section to provide fluid communication between the tubular main wall and the tubular extents.

In one aspect of the present invention, the prosthesis has a radius of curvature of the main elongate wall of from about 20 mm to about 80 mm creating an arc of about 15 to 90 degrees. Moreover, the lateral wall portions of the first open end, the apical region and the second open end of the prosthesis may be substantially planar or may be skewed from about 2 degrees to about 30 degrees.

In another aspect of the present invention, an arched implantable textile prosthesis is provided. The prosthesis includes a first woven section having an elongate tubular main wall with a first and a second open end defining a fluid passageway therethrough. The first woven section is arched to define an apical region of the main tubular wall with a radius of curvature from about 150 mm to about 300 mm. The first woven section can be further manipulated during implantation to a radius of curvature of from about 20 mm to about 80 mm to conform generally to an aortic arch of a patient without kinking of the tubular main wall. The prosthesis also includes a plurality of elongate woven tubular extents extending vertically from the top wall portion at the apical portion of the tubular main wall. These tubular extents are sutured to the first woven section to provide fluid communication between the tubular main wall and the tubular extents.

In yet another aspect of the present invention, a method for producing anatomically curved or significantly arched tubular prostheses is provided. The method includes weaving a first woven section having an elongate tubular main wall having a first and a second open end defining a fluid passageway therethrough; providing a curved mandrel having a radius of curvature generally conforming to the curve of an aortic arch of a human patient; placing the first woven section over the mandrel; heat setting the first woven section to set the shape of the first woven section; and removing the first woven section from the mandrel to provide an anatomically curved tubular main wall. Alternatively, the arched tubular prosthesis is woven into the anatomically curved shape.

In yet another aspect of the present invention, there is provided a method of treating a patient in need of an aortic arch prosthesis comprising an anatomically curved or significantly arched tubular prosthesis having a main tubular portions having opposed open ends and lateral tubular branches; preparing portions of an aorta of the patent for surgery and reception of the prosthesis; connecting one end of the main tubular portion to the descending aorta; connecting the aortic arteries to the lateral tubular branches; and connecting the other end of the main tubular portion to the ascending aorta to provide fluid communication among the ascending aorta, the aortic branches and the descending aorta.

DETAILED DESCRIPTION OF THE INVENTION

The present invention is directed to a vascular prosthesis which is useful in repair or replacement of a branched section of a blood vessel, and provides a textile vascular graft which is substantially fluid-tight and which is particularly useful in branched end-to-side anastomoses.

The prosthesis of the present invention is constructed of a textile material. Textile materials, for example textile tubular prostheses which are woven, knitted and/or braided, have gained widespread use as implantable tubular prostheses. In particular, woven or knitted textile tubular prostheses which are manufactured using tubular flat-weaving techniques are a common implant material for vascular grafts.

In tubular textile manufacturing processes, a variety of yarns are interlaced to create a tubular product. For example, a set of warp yarns is used which represents the longitudinal axis of the product being manufactured, and a fill yarn is interlaced in a transverse relation between the warp yarns. The fill yarn is continuously interlaced across the length of the warp yarns to form a tubular textile structure. Such manufacture will be discussed in more detail herein.

Figure 1:
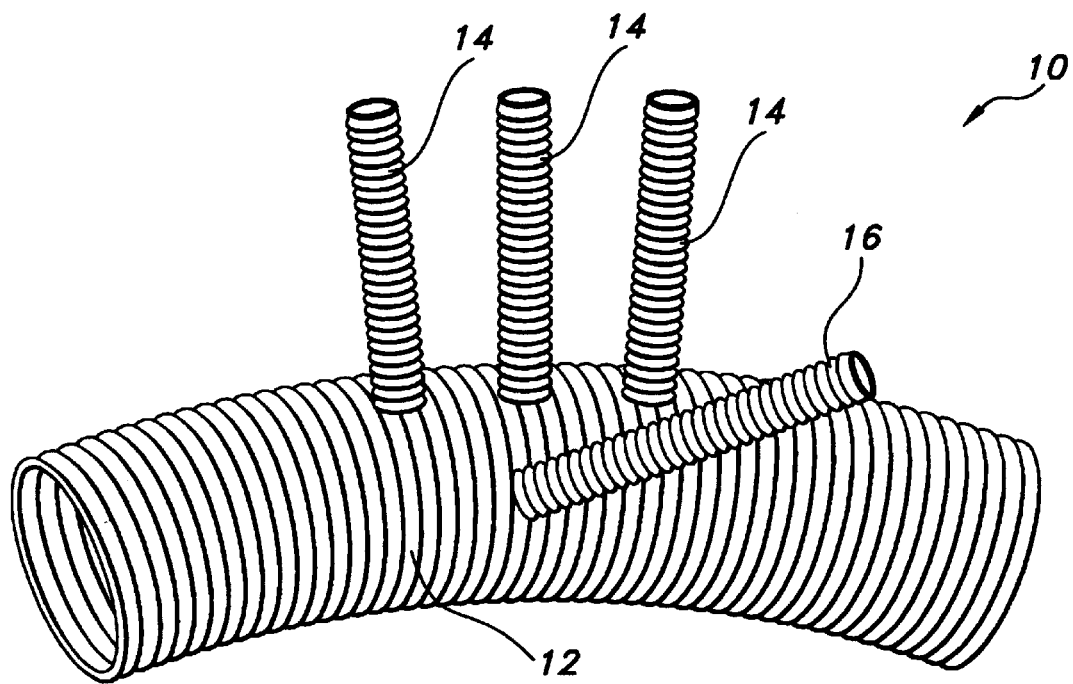
FIG. 1 is a perspective view of a conventional prior art aortic graft.
Figure 2:
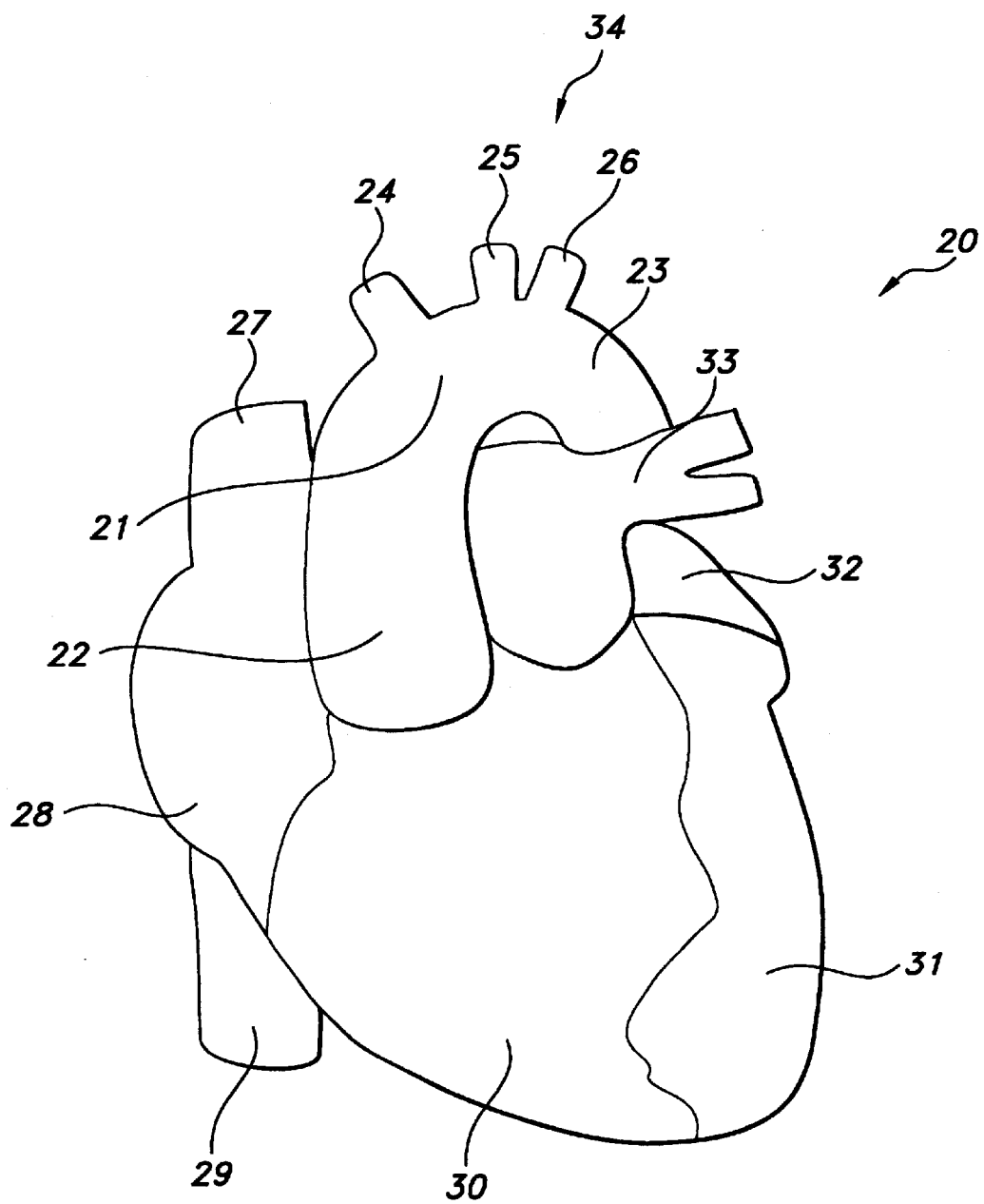
FIG. 2 is an illustration of a patient's heart and surrounding vessels, including an aortic arch.

FIG. 2 is an illustration of a human heart 20 and proximal arteries and vessels, interrelated as shown. Heart 20 includes right ventricle 30 and left ventricle 31. Also shown are superior vena cava 27, pulmonary aorta 33, left atrium 32, inferior vena cava 29, right atrium 28 and aorta 34. Aorta 34 includes ascending aorta 22, aorta arch 21 and descending aorta 23. The brachiochephalic (trunk) artery 24, left common carotid artery 25 and left subclavian artery 26 branch off from the aortic arch 21 as shown. The ascending aorta 22 is about 5 centimeters in length and commences at the upper part of the base of the left ventricle 31. The ascending aorta 22 then passes obliquely upward, forward and to the right to form a union with the aortic arch 21. The aortic arch 21 runs upward at first, then downward and to the rear. The aortic arch forms two curvatures, one with its convexity upward and the other with its convexity forward. The aortic arch 21 varies from about 2 to about 7 centimeters in length.

Figure 3:
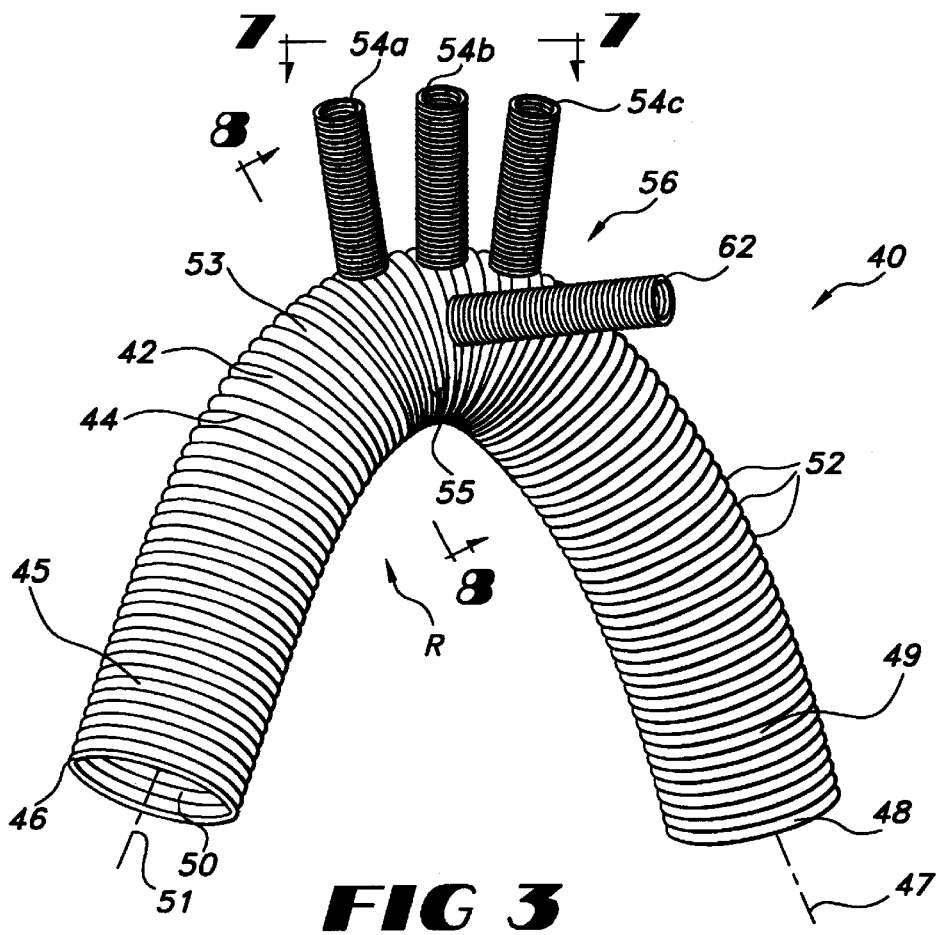
FIG. 3 is a perspective view of a textile vascular graft according to the present invention having a substantially anatomically arched shape.

An anatomically curved graft or prosthesis 40 according to the present invention for implantation at the aortic arch region is shown in FIG. 3. The anatomically curved graft 40 includes generally arched tubular main portion 42 having an elongate tubular main wall 44. Arched tubular main portion 42 further includes first open end 46 and opposed open end 48, with a main lumen 50 extending therethrough. Arched tubular main portion 42 is desirably of a generally constant internal diameter along the length thereof.

Arched tubular main portion 42 is constructed so as to repair or replace a damaged portion of an aorta in an adult mammal. Accordingly, arched tubular main portion 42 includes an internal diameter appropriately sized for such use, for example, approximately 26 to 30 millimeters. Alternatively, arched tubular main portion 42 may be constructed with an internal diameter which varies along the length thereof.

Arched tubular main portion 42 may be constructed of any known textile material. For example, arched tubular main portion 42 may be a textile material selected from woven material, knitted material, braided material, and the like. Combinations of such textile types may be employed. Desirably, arched tubular main portion 42 is a woven textile material. Additionally, the textile material may include a velour inner and/or outer surface, for instance, to facilitate tissue ingrowth and cell attachment thereto. Moreover, mixtures of yarn types may be employed to impart various properties, for example self-supporting properties, increased rigidity, increased flexibility, ravel resistance, as well as other desirable properties.

The arched tubular main portion 42 is generally configured to resemble the natural arch of the aorta. The anatomically curvature of the graft is accomplished, in part, by providing arched tubular main wall 44 with crimps 52. Additionally, such an arch is provided by incorporating heat-settable material into the textile material of tubular main portion 42 and heat setting the graft on a curved mandrel (not shown) having the desired arcuate angle.

The arched tubular main portion 42 is shaped so as to have a generally U-shaped configuration. Desirably, the arched tubular main portion 42 is shaped to substantially match the anatomical curve of the aortic arch. Typically, a patient's aortic arch has a radius of curvature from about 20 millimeters to about 80 millimeters and prosthesis 40 is generally so configured as shown by the radius of curvature "R" in FIG. 3. Radii of curvature from about 30 mm to about 70 mm are also useful. Moreover, radii of curvature from about 40 mm to about 60 mm are also useful with the practice of the present invention. As used herein the phrase "radius of curvature" and its variants refer to a radius of the circle whose curvature matches that of a curve at a particular point. For example, a curve having a length "L" can be represented by a segment of circle having a radius "R" and a central angle of "α", where L=R*α and where α is in radians. Thus, the radius of curvature may be used to define or approximate a two-dimensional curve because the length of the curve at a particular desirable point is known or is readily measurable. Desirably, arched tubular main portion 42 has a radius of curvature, R, from about 20 mm to about 80 mm to conform generally to an aortic arch of a patient. The radius of curvature, R, need not be constant along the length of tubular main portion 42, but could vary along the length thereof to reach an arcuate shape of desirable configuration. For example, tubular main portion could be shaped from several segments (not shown) each having a different radius of curvature, R.

Furthermore, the main tubular walls 45 and 49 beyond the arched tubular main portion 42 are also configured to substantially match the curvature of at least part of the ascending aorta 22 and/or part of the descending aorta 23. For example, the prosthesis 40 is generally U-shaped such that the first open end 46 or its axial axis 51 is disposed at an angle from about 135 degrees to about 225 degrees relative to an axial direction defined by the axial axis 47 at the second open end 48. Desirably, the first open end is disposed at about 180 degrees from the second open end. As such the arched tubular main portion 42 is shaped to follow the anatomical curvature of the aortic arch and the main tubular walls 45 and 49 are further configured into a generally U-shape to follow the anatomical curvature of the aorta beyond the aortic arch region.

Figure 4B:
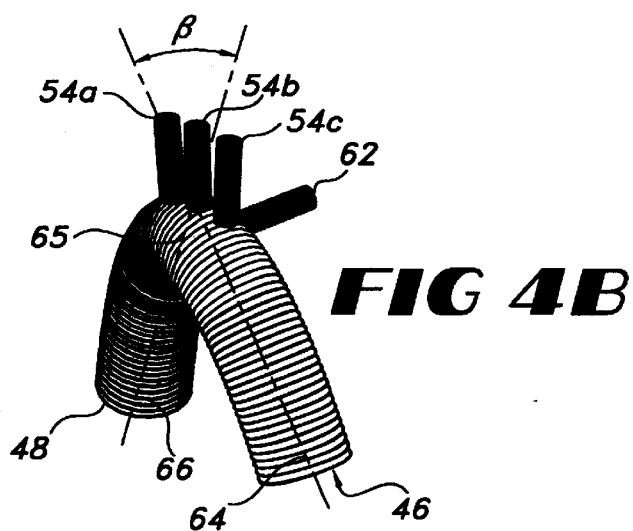
FIG. 4B is an alternate perspective view of the graft of FIG. 4A showing skewed ends of the graft.
Figure 4A:
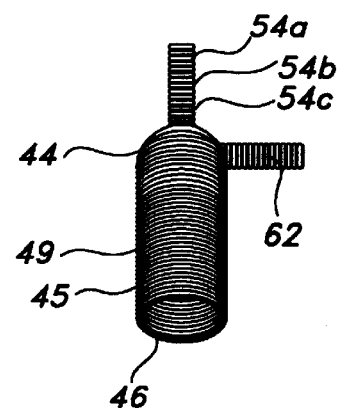
FIG. 4A is a side perspective view of the graft of FIG. 3.

Moreover, the prosthesis of the present invention may have non-skewed ends as shown in FIG. 4A or skewed ends as illustrated in FIG. 4B. As shown in FIG. 4B, the first open end 46 is skewed at an angle β from the second open end 48. The degree of skewing is typically from about 2 degrees to about 30 degrees. The degree of skewing may desirably be about from to 10 degrees to about 20 degrees. A skewing of about 15 degrees is also useful with the practice of the present invention. The degree of skewing, β, may be defined at a vertex of a geodesic line from lateral portion 64 of the first open end 46 to a lateral portion 65 of the apical region 56 with a geodesic line from the lateral portion 66 of the second open end 48 to the lateral portion 65 of the apical region 56. As used herein, the term geodesic and its variants refer to the shortest line between two points on a curve. Furthermore, as used herein, the term vertex and its variants refer to the point at which two lines intersect and the angle, such as β, formed thereat between the two lines. Alternatively, as shown in FIG. 4A, the lateral wall portions of the arched tubular main wall 44 and the tubular main walls 45 and 49 of open ends 48 and 46 are substantially planar.

The anatomically curved graft 40 further includes a plurality of elongate tubular branches 54a, 54b and 54c, extending from the tubular main wall 44. Desirably, the elongate tubular branches 54a, 54b and 54c extend from a top wall portion 53 of the apical region 56 of the arched tubular main portion 42. Tubular branches 54a, 54b and 54c may extend from the tubular main wall 44 at any angle with respect thereto. Desirably, tubular branches 54a, 54b and 54c extend substantially perpendicularly or vertically from the top wall portion 53 of the apical region 56 of the arched tubular main portion 42.

Figure 7:
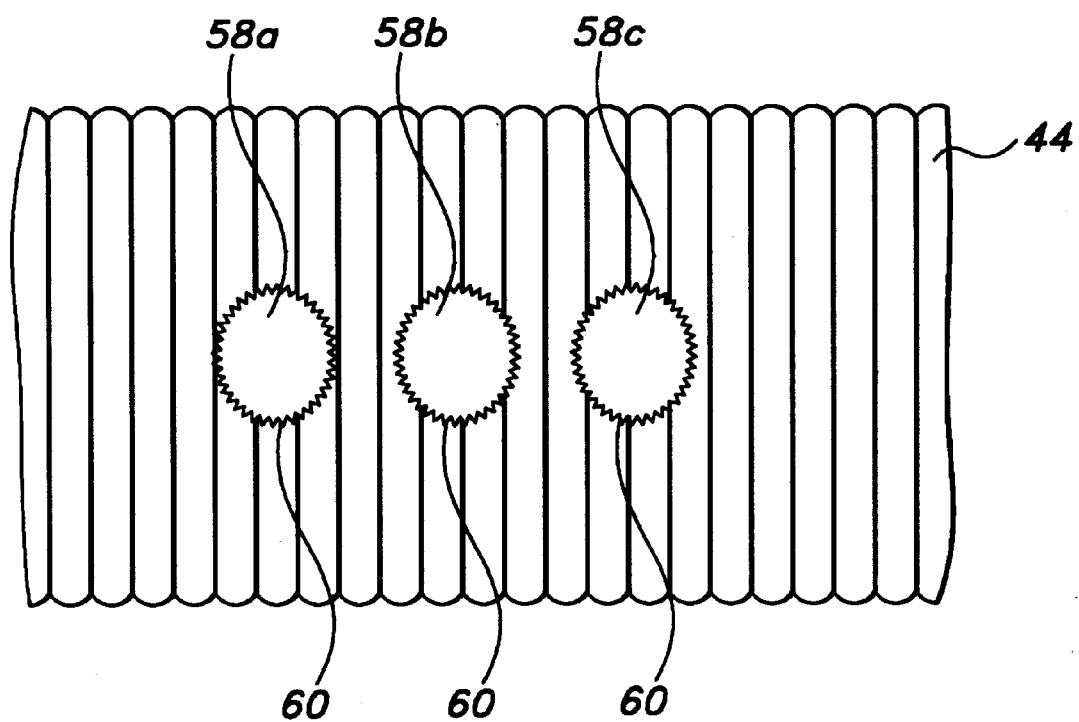
FIG. 7 is a top view of a portion of the graft of FIG. 3 taken along the 7—7 axis.
Figure 8:
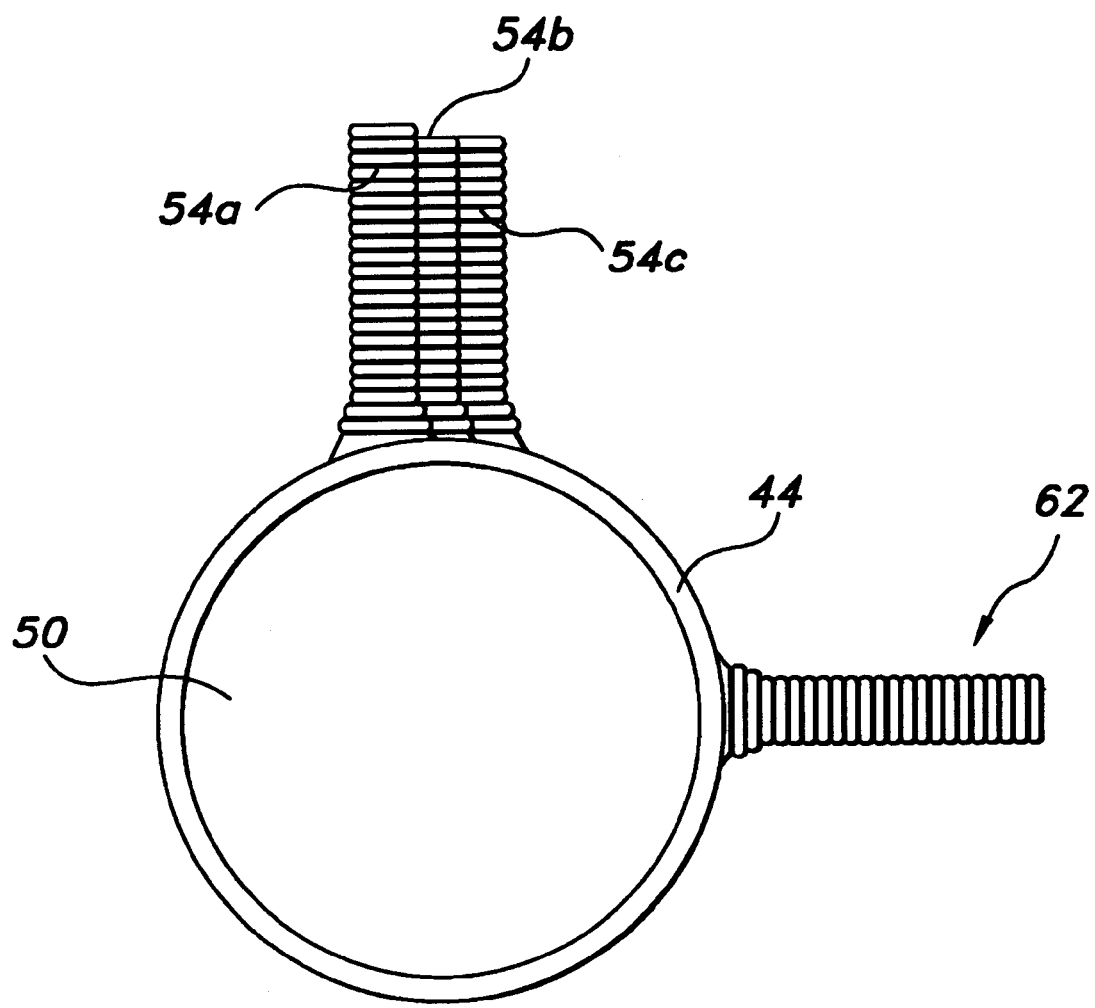
FIG. 8 is a cross-sectional view of a graft useful with the practice of the present invention taken along the 8—8 axis.

Elongate tubular branches 54a, 54b and 54c are desirably equally spaced along an axis with respect to arched tubular main portion 42, as depicted in FIG. 7 which shows holes 58a, 58b and 58c in main tubular wall 44. Tubular branches 54a, 54b and 54c are securably attached to wall portions proximal to the holes 58a, 58b and 58c. One means of such attachment is through the use of sutures 60, but other attachment techniques, such as bonding, may suitably be used. Alternatively, elongate tubular branches 54a, 54b and 54c may be axially spaced and circumferentially offset with respect to the tubular main wall 44 of the arched tubular main portion 42, as depicted in FIG. 8.

Elongate tubular branches 54a, 54b and 54c may be of the same length as shown in FIG. 3, or may be of different lengths independently. Furthermore, each of elongate tubular branches 54a, 54b and 54c include a generally constant internal diameter along the length thereof. Elongate tubular branches 54a, 54b and 54c may be of the same internal diameter, or may be of different internal diameters independent of one another. For example, elongate tubular branches 54a, 54b and 54c may all have the same constant internal diameter of approximately 8 millimeters. Alternatively, elongate tubular branches 54a, 54b and 54c may each have different internal diameters. For example, elongate tubular branch 54a may have an internal diameter of approximately 10 millimeters, while elongate tubular branches 54b and 54c may have an internal diameter of approximately 8 millimeters.

Tubular port 62 is provided as a procedural aid, for example as an access port to a heart-lung machine, for use during surgical implantation procedures. For example, oftentimes it is desirable to access main lumen 50 of the graft 40 during a surgical procedure from outside of the body. Tubular port 62 provides a means for such access. Tubular port 62 is not meant for anastomosis to any part of the body, but is provided for temporary use during a surgical procedure. After completion of an implant procedure, tubular port 62 is often ligated and tied off, for example by way of sutures, to provide a completely closed main lumen 50.

Desirably, tubular port 62 extends laterally from tubular main wall 44 at lateral or sidewall portion 55 near the apical region 56. Such a location is typically remote from tubular branches 54a, 54b and 54c. Other locations for the tubular port 62 may suitably be used. Furthermore, tubular port 62 desirably extends substantially perpendicularly from tubular main wall 44 at a 90° angle with respect to vertically extending tubular branches 54a, 54b and 54c.

As with the arched tubular main portion 42, tubular branches 54a, 54b and 54c and tubular port 62 may also be constructed of any known textile material. For example, tubular branches 54a, 54b and 54c and tubular port 62 may be a textile material selected from the group consisting of woven material, knitted material, braided material, and the like. Desirably, arched tubular main portion 42, tubular branches 54a, 54b and 54c and tubular port 62 are constructed of similar textile material, for instance, woven textile material.

Graft 40 is desirably capable of maintaining fluid-tight lumens at the time of implantation. In order to control the porosity of graft 40, a natural or synthetic sealant may be incorporated into the textile structure, as is known in the art. For example, collagen may be incorporated into the textile structure of graft 40 to act as a sealant. Such collagen is typically resorbed by the body over time, and is replaced with native tissue, which further serves to anchor graft 40 in place within the body. For example, U.S. Pat. Nos. 4,842,575 and 5,108,424, both of which are incorporated herein by reference, may be employed to provide collagen to graft 40.

In another aspect of the present invention, an arched implantable textile prosthesis that has less curvature than that of the aortic arch is provided. In this aspect of the present invention the radius of curvature, "R", of prosthesis 40 is greater than the radius of curvature of the aortic arch or greater than 80 millimeters. Desirably, prosthesis 40, and in particular main tubular wall 44, has a radius of curvature from about 150 millimeters to about 300 millimeters. Prosthesis 40 can then be further manipulated by a surgeon to conform to the curvature of the aortic arch without kinking of the main tubular wall 44. As such, prosthesis may be described as an arched prosthesis which upon further bending of the prosthesis 40 to an anatomically desirable or optimum curvature, such as the curvature of the aortic arch, does not exhibit kinking of its main tubular wall 44. Grafts in the prior art the were straight or just slightly arched, i.e., having a radius of curvature substantially greater than about 300 millimeters, would kink upon such manipulation by a surgeon to achieve the anatomically desirable degree of curvature. In contrast, grafts of the present invention allow the surgeon to tailor the graft to the aortic arch of the individual patient either before or during implantation.

Having described the prosthesis of the present invention, its construction and manufacture will now be discussed. As noted, the prosthesis of the present invention is constructed of textile material, such as a woven, knitted or braided material. Such textile materials are particularly useful in vascular graft applications, in that the textile pattern of the material can be constructed to be very pliable and capable of permitting sufficient ingrowth of surrounding tissue, while also being capable of maintaining a fluid-tight, i.e., blood-tight wall structure.

The textile prosthesis of the present invention is desirably a woven material, and can be flat woven using any known weave pattern, including simple weaves, basket weaves, twill weaves, velour weaves and the like. For example, in one particularly desirable woven graft, the textile prosthesis maybe woven using a flat plain tubular weave pattern with about 100–200 warp yarns per inch per layer and about 70–120 fill yarns per inch per layer. Desirably, the textile prosthesis is woven with about 170–190 warp yarns per inch per layer and about 86–90 fill yarns per inch per layer. The wall thickness of the graft may be any conventional useful thickness, but is desirably no greater than about 1.0 mm. A useful wall thickness includes, but is not limited to, from about 0.10 mm to about 0.75 mm.

Any type of textile product can be used as the yarns or fibers of the present invention. Of particular usefulness are synthetic materials such thermoplastic polymers. Thermoplastic yarns suitable for use in the prostheses of the present invention include, but are not limited to, polyesters, polypropylenes, polyethylenes, polyurethanes, polytetrafluoro-ethylenes and mixtures thereof. The yarns may be of the monofilament, multifilament or spun type.

The yarns used in forming the grafts of the present invention may be flat, twisted or textured, and may have high, low or moderate shrinkage properties. Additionally, the yarn type and yarn denier can be selected to meet specific properties for the prosthesis, such as porosity, flexibility and compliance. The yarn denier represents the linear density of the yarn (number of grams mass divided by 9,000 meters of length). Thus, a yarn with a small denier would correspond to a very fine yarn whereas a yarn with a larger denier, e.g., 1000, would correspond to a heavy yarn. The yarns used in the prosthesis of the present invention may have a denier from about 20 to about 1000. Useful deniers also include from about 40 to about 300. Desirably, the warp and fill yarns are polyester type yarns. Warp and fill yarns that are one ply, 50 denier, 48 filament flat polyester are also useful with the practice of the present invention.

Prosthesis 40, and in particular tubular main portion 42 and tubular branches 54, 56 and 58 are independently constructed of woven textile material. Woven tubular textile products are particularly useful in manufacturing vascular graft products in that a variety of unique shapes and sizes can now be accomplished. For example, tubular main portion 42 may then be fitted onto a mandrel in a desired shape and may be heat-shrunk to set the fibers of the fabric into the desired shape of the mandrel. Heat setting is a thermal process, as further described below, used to set the shape of a graft which has been placed on a mandrel.

Figure 5:
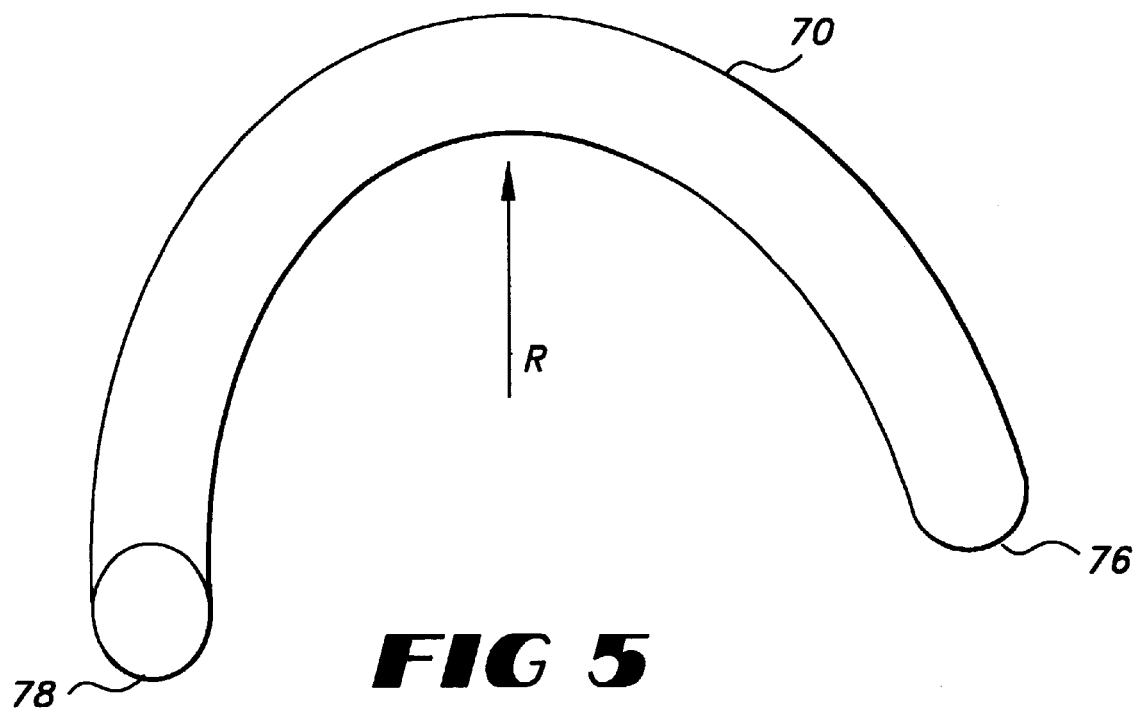
FIG. 5 is depiction of a curved mandrel useful with the practice of the present invention.
Figure 6:
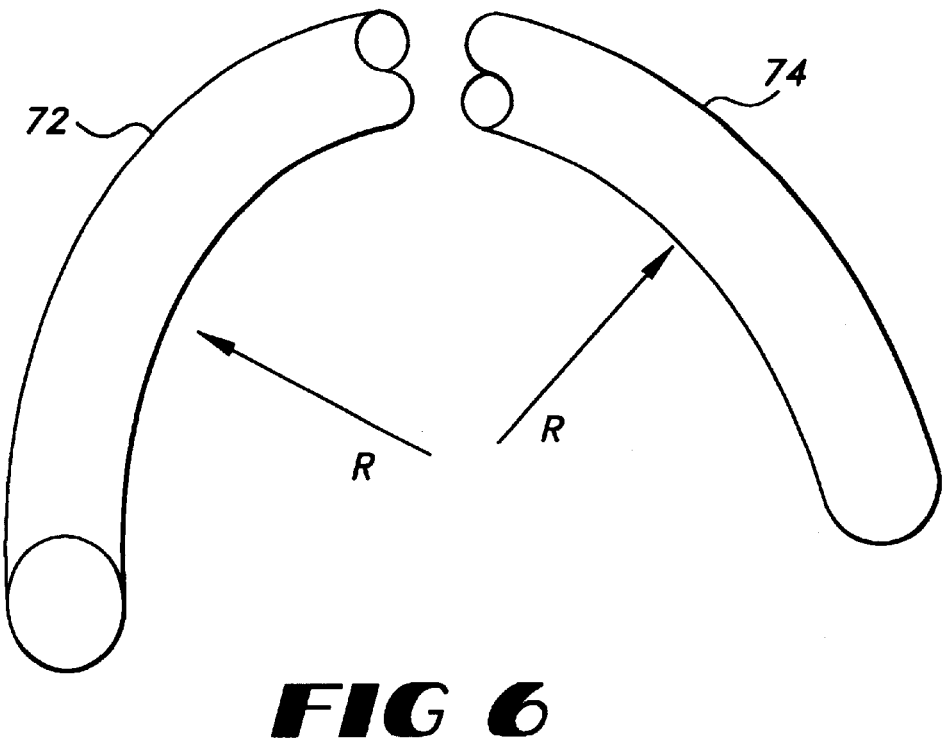
FIG. 6 is a depiction of a second curved mandrel useful with the practice of the present invention having releasable segments.

Upon removal from the mandrel, tubular main portion 42 is set to the desired shape which can include a two or three dimensionally arched shape as described above. For example, an arched mandrel 70, which is depicted in FIG. 5, may suitably be used to form the anatomically curved graft 40 of the present invention. Alternatively, as depicted in FIG. 6, mandrel portions 72 and 74 may be releasably joined to form the arched mandrel 70. After heat setting the tubular main portion 42, mandrel portions 72 and 44 are removed from one and the other to facilitate removal of the heat-set graft therefrom.

Alternatively, prosthesis 40 may be flat-woven into the general U-shape and then heat set on the arched mandrel 70 to set the textile fibers into the desired shape including a generally open tubular or cylindrical shape along the length of the prosthesis. Weaving such a shaped prosthesis is accomplished by selectively changing the number of warp and/or fill yarns in the weaving pattern. For example, the techniques of U.S. Pat. No. 5,800,514, which is incorporated herein by reference, gradually change the number of warp and/or fill yarns to, among other things, provide shaped, woven prostheses.

Desirably, the radius of curvature, R, of mandrel 70 is less than about 300 millimeters. More desirably, the radius of curvature is from about 20 millimeters to about 80 millimeters. Such radii of curvature yield a substantially anatomically curved graft, such as prosthesis 40, which can be implanted in most patients without fear of kinking or undesirable stress or contortion. Radii of curvature from about 150 to about 300 millimeters are also useful in setting the curvature for the arched prosthesis of the present inventions. Moreover, mandrel 70 may have a rearward curvature end 76 which is spatially behind end 78 to provide a degree of skewing, as describe above. The combination of the planar curvature and the rearward curvature or skewing of the mandrel produces a three-dimensionally anatomically curved graft.

The individual components of prosthesis 40, such as main tubular body 42, tubular branches 54a, 54b and 54c, and tubular port 62 may suitably be heat set on different mandrels (not shown) prior to the suturing of the tubular branches 54a, 5b and 54c and the tubular port 62 to the main tubular body 42. These different mandrels may be straight or may be curved, if desired.

As noted above, the tubular-woven graft of the present invention is desirably constructed of polyester which is capable of shrinking during a heat-set process. Such grafts or graft components are typically flat-woven in a tubular form. Due to the nature of the flat-weaving process, the tubular grafts are generally flat in shape after weaving. Such grafts, however, when constructed of shrinkable polyester yarn, can be heat set on a mandrel to form and hold a generally open tubular or cylindrical shape.

Such a heat-setting process is accomplished by first weaving the graft in a seamless tubular form out of a material capable of shrinking during a heat-setting or similar process. The graft may be preshrunk or compacted before it is placed on a mandrel. Preshrinking entails compressing the prosthesis longitudinally on the order of 25–50%. Preshrinking may be achieved by submitting the compressed graft to moderate temperatures, such as from about 190° F. to about 400° F. or more desirably from about 200° F. to about 235° F. Usually the graft is placed in a medium for the preshrinking. Such a medium can include without limitation hot water, a chemical fluid, such as methylene chloride, or a gas, such as air or carbon dioxide. The grafts of the present invention, however, may suitably be made without such a preshrinking of the yarns.

After the graft is woven or alternatively woven and preshrunk, the graft is placed on a mandrel having circumferentially directed grooves (not shown). A wheel is used to mechanically force the graft to the contours or grooves of the mandrel, resulting in circumferentially directed crimps. Desirably the grafts of the present invention have from about 10 to 30 crimps per inch of longitudinal graft length. The graft is heated to set the desired crimp pattern. Alternative, such grooves or crimps can be imported using compressive techniques as shown in U.S. Pat. Nos. 3,096,560; 3,142,067 and 5,697,970, the contents all of which are incorporated herein by reference.

After crimping the prosthesis of the present invention is placed on a curved mandrel and heated in an oven at a temperature and time capable of causing the yarns of the graft to heat set to the shape and diameter of the mandrel. Preferably polyester yarns are used and the heat setting is accomplished at time and temperatures appropriate for the material. For example, heat setting can be accomplished in a steam autoclave at about 190–400° F. for a period of about less than an hour. Temperatures in the range of 190° F.–300° F. are also useful. Desirably, temperatures from about 250° F. to about 260° F. are also useful. Desirably, time periods from about 5 to about 30 minutes are useful. More desirably, with time periods from about 10 to about 20 minutes are useful. Other methods of heat setting known in the art may be employed.

For implantation of the prosthesis 40 surgery is required. If a heart-lung machine is used during such surgery, tubular port 62 is used to provide fluid communication to the heart-lung machine. During surgery the aorta is opened along the length of the aortic arch. Any thrombus and debris is removed. An end-to-end anastomosis of prosthesis 40 is made to the descending aorta. The branches of the aortic arch are anastomosed to the tubular branches 54a, 54b and 54c. The other end of the prosthesis 40 is then sutured to the ascending aorta in an end-to-end fashion. Portions of the aortic arch may then be placed over the graft and sutured together to aid healing. The present invention is not limited to such surgical procedure and other techniques may suitably be used.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

An implantable textile prosthesis is anatomically curved to substantially match the natural curvature of the aortic arch in a human being or patient. The first woven section is arched define an apical region and to conform generally to an aortic arch of a human patient. A plurality of elongate woven tubular extents extend vertically from a top wall portion at the apical region of the tubular main wall. These tubular extents are sutured to the first woven section to provide fluid communication between the tubular main wall and the tubular extents.

What is claimed is:

1. An arched implantable textile prosthesis comprising:

a first woven section comprising an elongate tubular main wall having a first and a second open end defining a fluid passageway therethrough and further defining a lateral wall portion, a top wall portion and a bottom wall portion extending longitudinally therebetween, the first woven section being heat-settably arched with a radius of curvature from about 150 mm to about 300 mm defining an apical region of the main tubular wall between the first and second open ends; and a plurality of elongate woven tubular extents extending vertically from the top wall portion at the apical portion of the tubular main wall and being sutured to the first woven section to provide fluid communication between the tubular main wall and the tubular extents;

wherein the first woven section can be further arched to a radius of curvature of from about 20 mm to about 80 mm to conform generally to an aortic arch of a patient without kinking of the tubular main wall.

2. The prosthesis of claim 1, wherein the plurality of elongate tubular extents are spaced along an axis with respect to the tubular main wall.

3. The prosthesis of claim 1, wherein the plurality of elongate tubular extents are circumferentially offset with respect to said tubular main wall.

4. The prosthesis of claim 1, wherein the plurality of elongate tubular extents have substantially the same diameters.

5. The prosthesis of claim 1, wherein the plurality of elongate tubular extents have different diameters with respect to each other.

6. The prosthesis of claim 1, wherein the plurality of elongate tubular extents have substantially the same lengths.

7. The prosthesis of claim 1, wherein the plurality of elongate tubular extents have different lengths with respect to each other.

8. The prosthesis of claim 1, wherein the plurality of elongate tubular extents include at least three elongate tubular extents.

9. The prosthesis of claim 1, further including an elongate tubular port extending laterally from the tubular main wall at the lateral wall portion of the apical portion.

10. The prosthesis of claim 1, wherein the tubular main wall and the tubular branch extents are constructed of material selected from the group consisting of polyester, polypropylene, polyethylene, polyurethane, polytetrafluoroethylene and mixtures thereof.

11. The prosthesis of claim 1, wherein the lateral wall portions of the firs open end, the apical region and the second open end are substantially planar.

12. The prosthesis of claim 1, wherein the first and second open ends are skewed from about 2 degrees to about 30 degrees at a vertex of a geodesic line from the lateral portions of the first open end to the apical region with a geodesic line from the lateral portions of the second open end and the apical region.

* * * * *

UNITED STATES PATENT AND TRADEMARK OFFICE
CERTIFICATE OF CORRECTION

PATENT NO. : 6,770,090 B2
DATED : August 3, 2004
INVENTOR(S) : Gantt et al.

It is certified that error appears in the above-identified patent and that said Letters Patent is hereby corrected as shown below:

Title page,
Item [57], ABSTRACT,
Lines 1-3, should read -- An...prosthesis is provided...human being or patient. --.

Column 3,
Line 38, should read -- FIG. 5 is a depiction... --.

Column 4,
Line 54, should read -- The anatomical curvature of the... --.

Column 7,
Line 15, should read -- As such, prosthesis 40 may be... --.
Line 20, should read -- Grafts in the prior art were... --.

Column 8,
Line 53, should read -- ...skewing, as described above. --.
Line 61, should read -- ...branches 54a, 54b and 54c and the... --.

Column 9,
Line 28, should read -- Alternatively, such grooves or crimps... --.

Column 10,
Line 58, should read -- wall portions of the first open end... --.

Signed and Sealed this

Twelfth Day of October, 2004

JON W. DUDAS
*Director of the United States Patent and Trademark Office*